United States Patent [19]
Hussey

[11] Patent Number: 5,582,187
[45] Date of Patent: Dec. 10, 1996

[54] PROTECTIVE MASK

[76] Inventor: Cynthia L. Hussey, 1609 Stuart St., Berkeley, Calif. 94703

[21] Appl. No.: 419,723

[22] Filed: Apr. 10, 1995

[51] Int. Cl.$^6$ .................................................. A61F 11/00
[52] U.S. Cl. .......................... 128/857; 128/842; 128/859; 128/918
[58] Field of Search .................... 128/848, 857, 128/858, 859, 842, 844, 918; 2/2

[56] References Cited

U.S. PATENT DOCUMENTS

| | | | |
|---|---|---|---|
| 1,629,892 | 5/1927 | Storms | 128/848 |
| 1,775,718 | 9/1930 | Garvey | 128/848 |
| 1,986,988 | 1/1935 | Treadwell | 128/857 |
| 3,089,148 | 5/1963 | Grossberg | 2/206 |
| 3,288,138 | 11/1966 | Sachs | 128/139 |
| 4,084,585 | 4/1978 | Venaleck | 128/146 |
| 4,323,063 | 4/1982 | Fisichella | 128/139 |
| 4,671,271 | 6/1987 | Bishop et al. | 128/206 |
| 4,815,456 | 3/1989 | Rubin et al. | 128/859 |
| 4,856,509 | 8/1989 | Lemelson | 128/206.19 |
| 4,949,731 | 8/1990 | Harding | 128/842 |
| 4,974,605 | 12/1990 | Esqueda | 128/857 |
| 5,016,649 | 5/1991 | Johnson | 128/859 |
| 5,303,423 | 4/1994 | Gazzara | 128/857 |
| 5,320,112 | 6/1994 | Bloodsaw | 128/842 |
| 5,388,592 | 2/1995 | Williams | 128/842 |
| 5,390,681 | 2/1995 | Daley | 128/842 |

FOREIGN PATENT DOCUMENTS

| 0459104 | 4/1928 | Germany | 128/848 |
|---|---|---|---|

OTHER PUBLICATIONS

Oradam™ Latex Shields, Manufactured by Oasis Latex of Pomona, CA (no written material available).

*Primary Examiner*—Michael A. Brown

[57] ABSTRACT

A thin, flexible shield for the mouth to protect against transmission of STDs (Sexually Transmitted Diseases) during cunnilingus and oral-anal sex. A shield (32) is held over the mouth either alone or in a holder assembly (44) by mounting devices which retain the mask against the face of the user. The holder assembly (44) may consist of one or two rings (30U, 30L) interlocked with each other or with the shield to grip the shield.

19 Claims, 2 Drawing Sheets

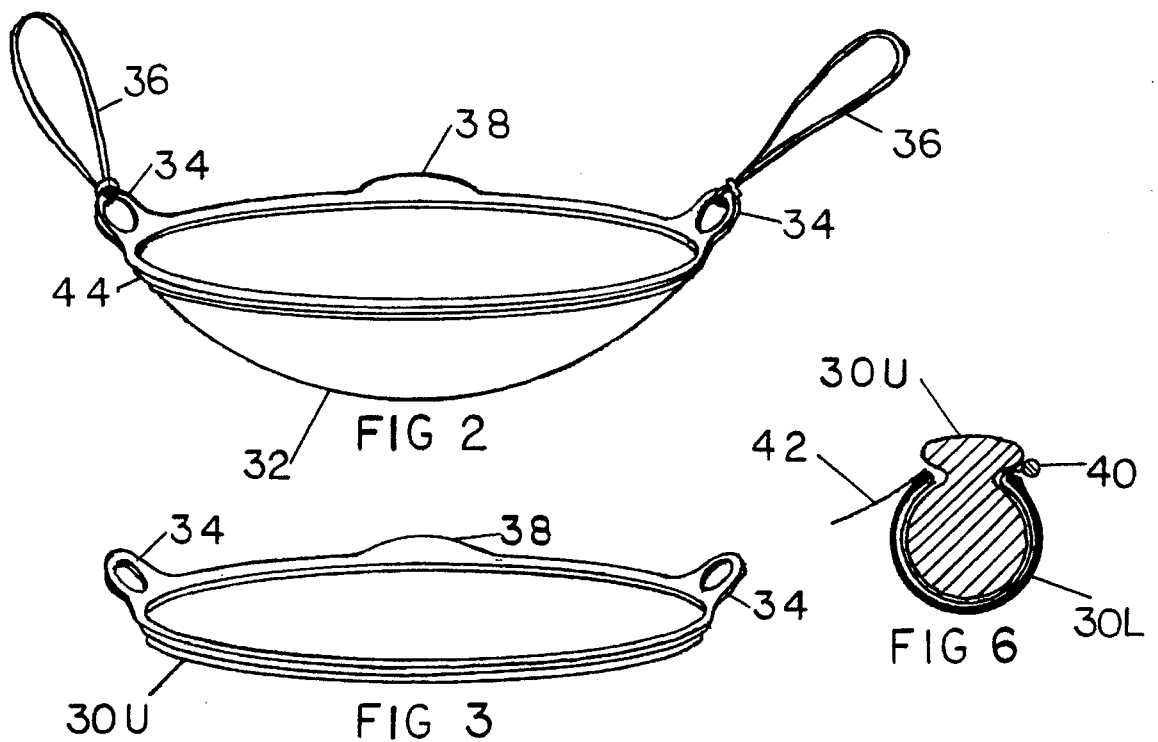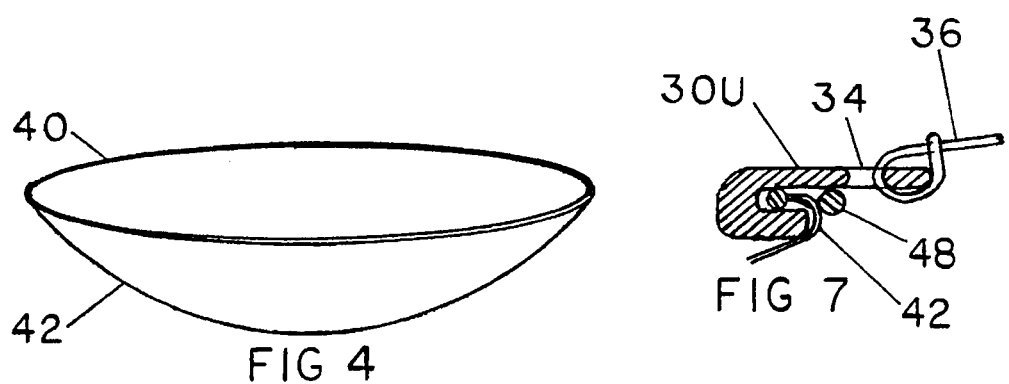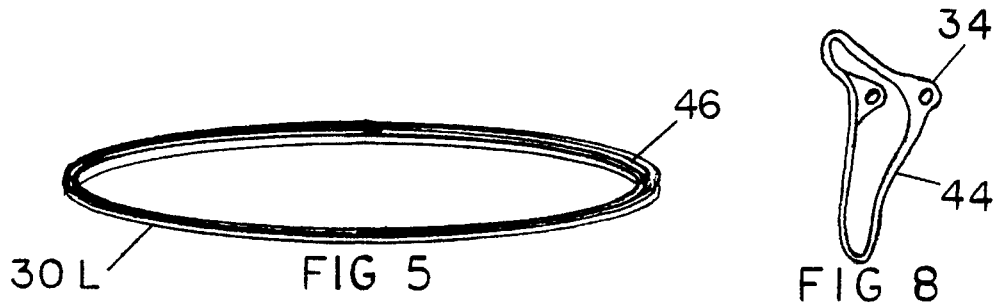

PROTECTIVE MASK

BACKGROUND—FIELD OF INVENTION

This invention relates to prophylactics, specifically to a protective covering for the mouth to prevent the transmission of diseases during oral sex.

BACKGROUND—DISCUSSION OF PRIOR ART

The need for adequate protection against the transmission of diseases between sexual partners is obvious. Many infectious diseases have been spreading, affecting an increasing number of people. While condom use is increasing, condoms cannot provide adequate protection for certain other sexual activities in which consenting adults might engage. Cunnilingus and oral-anal sex are two of those activities.

Currently there are two items commonly used for protection during these activities: plastic wrap and dental dams. Plastic wrap is thinner than dental dams, but it has serious disadvantages when held against a partner's body for oral sex. It generally becomes quite wrinkled, making it difficult to find and properly stimulate the clitoris during cunnilingus. It causes difficulties with breathing because it gets sucked onto the nostrils, causing a suffocating feeling. It can also unfortunately stimulate a gag reflex when part of it is sucked into the mouth during sex. It can require one of the hands to hold it against the partner's body, meaning that hand is not free for other kinds of concurrent stimulation.

Dental dams do not wrinkle as much as plastic wrap when used for this purpose, but they suffer from all of the other disadvantages. Dental dams are also thicker than plastic wrap, causing great difficulty in locating and stimulating the clitoris. In addition, dental dams also often come with distinctly unappealing artificial flavors, which may cause gag reactions in some people. There is currently available a holder for the dental dams consisting of straps which go around the legs of the partner and hold the dam in place on the body. This does free the hands, but does not alleviate the other problems. In addition, it can be tricky to ensure that the dental dam remains in place to prevent any contact of the mouth with the partner's body.

Two products are currently commercially available which attempt to surmount some of these disadvantages, ORADAM™ latex shields, manufactured by Oasis Latex, Inc, of Pomona, Calif., and Eros Veils, manufactured by Tracey Williams of San Francisco, Calif.

ORADAM™ latex shields are made of rubber latex molded into a distendable sheath that encircles the head from just under the nose to below the chin and extends around the back of the head. They have a protruding portion to receive the extended tongue of the user. While they have the advantage of being relatively thin compared with traditional dental dams, ORADAM™ latex shields suffer from several disadvantages.

Putting on the ORADAM™ latex shield is difficult. It is tight and difficult to get around the back of the head. It tends to roll up and get tangled in the hair, pulling the hair and causing pain. It is difficult to position it properly under the nose, and difficult to maintain in this position. Once on, it is very tight and uncomfortable. It is quite clingy, making it very hard to open the mouth with it in place. Encasing the tongue in the protrusion causes gagging for some people. With the tongue encased, movements of the tongue and mouth have a tendency to pull the ORADAM™ latex shield out of place, off of the upper lip and into the mouth. This renders it useless for protection.

Eros Veils, U.S. Pat. No. 5,388,592 (1995), by Tracey Williams, are made of a very thin plastic and come in four shapes: mask, brief, hourglass, and rectangular. The extreme thinness of Eros Veils does make it much easier to locate and stimulate sensitive areas. The fairly simple designs are cut out of flat material, instead of being molded. In addition to these advantages, however, they suffer from several disadvantages.

Although according to their use directions Eros Veils are designed to stay in place on moistened skin, in actual use Eros Veils do not stay in place on the skin so readily. They slip out of place and require a hand to keep them in place.

Two shapes suffer from specific disadvantages: the mask and the briefs.

The Eros Veil mask is a flat elongated oblong with slots for the ears and an extension downward to cover the chin. It is designed to cover the area from just under the nose to under the chin and up along the cheeks to the ears. This mask design suffers several disadvantages. It is tricky to get the ears properly placed through the slots. The slots are small and must be stretched to get the ears completely through. Even once the slots are properly fitted onto the ears, the mask has a tendency to slip around. It doesn't stay firmly in place: it slips up over nose, causing difficulty in breathing. It also slips off of the mouth., rendering it useless for protection. It also has a tendency to be sucked up into the mouth, causing gagging for some people.

The Eros Veil briefs are designed to be worn on the body of the partner receiving stimulation. They have many disadvantages. They slip around on the body. Maintaining proper placement between the mouth and the body is almost impossible without using a hand to hold it in place. Like the mask and plain plastic wrap, the briefs have a tendency to be sucked up into mouth, causing gagging for some people.

The Eros Veils hourglass and rectangular shields are simply flat and cut in those shapes. They suffer from all the same disadvantages as regular plastic wrap.

All these disadvantages might tend to lead some people to dispense with any sort of protection for cunnilingus, but protection is still needed. Beyond the devastating threat of AIDS there are still further infections that need to be guarded against: herpes, gonorrhea, syphilis, chlamydia, condiloma, candida, etc. Some of these are curable now, but may go undetected for a long time, causing serious damage before treatment. The currently incurable ones must be guarded against with every precaution, to prevent the spread of misery.

Several prior attempts have been made to provide protection for oral sex which may have effectiveness in preventing the transmission of disease, but are not particularly practical for general production and use.

Esqueda, in U.S. Pat. No. 4,974,605 (1990), proposes a facial prophylactic consisting of a thin membrane molded to conform to the face and covering the entire facial area from below the chin to the bridge of the nose. It further proposes a system of breathing tubes imbedded in the mask to facilitate respiration.

Bishop et al., in U.S. Pat. No. 4,671,271 (1987), propose a protective facial mask which is very similar to Esqueda. It covers the same facial area and includes breathing tubes, although its construction is more like a tube, a sheath which slips over the head with the back section cut to form two straps.

Johnson, in U.S. Pat. No. 5,016,649 (1991), proposes a protective mask consisting of a thin membrane which is generally flat and wraps around the face to cover the facial area from below the chin to just under the nose.

Bloodsaw, in U.S. Pat. No. 5,320,112 (1994), proposes an oral condom which is generally oblong with lateral portions extending upward over the cheeks toward the ears. It utilizes a pair of molded earpieces to attach it to the user's head. It covers the area from just under the nose to under the chin and includes a protruding portion designed to conform to the shape of the lips and extended tongue of the wearer.

Harding, in U.S. Pat. No. 4,949,731 (1990), proposes an oral prophylactic which is molded to the general shape of the open mouth and the tongue with a labial portion that extends just over the lips of the wearer. It is inserted into the mouth, having a deep pouch that coats the inside of the mouth, and it is secured to the outside of the mouth with adhesive or a headband.

Venaleck, in U.S. Pat. No. 4,084,585 (1978), proposes a face mask, and Rubin et al., in U.S. Pat. No. 4,815,456 (1989), propose an hygienic device, both of which are similar to the Eros Veil mask in that they are generally flat and elongated, with slits or holes for the ears, although Rubin does specify a generally conical protrusion in the central portion of the mask to receive the tongue.

Daley, in U.S. Pat. No. 5,390,681 (1995), proposes a prophylactic device for oral sex designed to be held by the hands of the user in proper placement against the body of the partner receiving stimulation, and consists of an oval barrier with a central conical protrusion to receive the tongue.

Esqueda, Bishop, and Johnson suffer from similar disadvantages:

(a) They have a distinctly surgical appearance which is unappealing for use during sex.

(b) They are designed to cover far more than the area needed for adequate protection during oral sex, therefore wasting considerable materials.

(c) They are expensive to make because of the large area covered, and in the case of Esqueda and Bishop because of the eccentricity of the shape. This cost makes them unlikely to be made and used as disposable articles, but to provide the protection they were designed for, they must be used only once.

(d) They are tricky to put on. Esqueda and Johnson require placing them on the face and then tying or slipping on two separate ties or bands to keep them in place. Bishop requires slipping a tight tube over the head, much like the ORADAM™ latex shield, tangling and pulling hair.

In addition, Johnson suffers because, as with the Eros Veil mask, it is difficult to maintain in the proper position over the mouth during use, and the loose central portion of it may be easily sucked up into the mouth during use, causing gagging and difficulty in swallowing.

Further, the Esqueda Facial Prophylactic and the Bishop Protective Facial Mask suffer because their breathing tube systems are tricky and costly to implement and may give their wearers a sense of suffocation or claustrophobia.

Bishop also appears to be very tight, like the ORADAM™ latex shield, probably causing discomfort and significantly inhibiting the movements of the jaw, lips, and tongue of a wearer.

Bloodsaw suffers from these disadvantages:

(a) As with the ORADAM™ latex shields, having the tongue encased in the protruding portion is likely to stimulate the gag reflex for some people and cause difficulty in swallowing.

(b) Also as with the ORADAM™ latex shields, having the tongue in the protruding section while moving the mouth and tongue is likely to dislodge the upper section of the condom from its place over the upper lip.

(c) Like Esqueda, it is expensive to make because of the eccentricity of its shape.

Harding suffers from these disadvantages:

(a) It may slip out of place quite easily, rendering it useless for protection.

(b) The idea of using adhesives around the outside of the lips to attach it is distasteful.

(c) It may trigger a gag reflex for some people by coating the inside of the mouth.

(d) By its shape it may limit the freedom of movement of the tongue and lips of the wearer.

(e) When in place inside the mouth, it can cause difficulties in swallowing.

(f) It does not offer adequate coverage of the skin area immediately surrounding the lips, since it only just barely covers the lips.

(g) It is tricky to apply correctly to provide ample covering for the lips.

(h) Its shape is difficult and costly to manufacture, especially for a disposable item.

Venaleck and Rubin both suffer from disadvantages similar to those of the Eros Veil mask, specifically:

(a) It is difficult to get the ears properly placed through the slots.

(b) Even once the slots are properly fitted onto the ears, the masks tend to slip out of place, up over the nose, causing difficulty in breathing.

(c) They also could easily slip off part of the mouth, leaving the user vulnerable to infection.

(d) They also tend to be sucked up into the mouth, causing gagging for some people.

Since it includes a tongue protrusion, Rubin suffers additional disadvantages similar to those of the ORADAM™ latex shield:

(e) Encasing the tongue in the protrusion causes gagging for some people and difficulty in swallowing.

(f) With the tongue encased, movements of the tongue and mouth tend to pull the mask out of place, off of the upper lip and into the mouth. This renders it useless for protection.

Daley suffers from these disadvantages:

(a) Encasing the tongue in the protrusion causes gagging for some people.

(b) Encasing the tongue in the protrusion may cause difficulties in swallowing.

(c) Part of the shield or the tongue protrusion portion may be easily sucked into the mouth, causing gagging.

(d) Since it must be held in place by the hands of the user, the hands are then unavailable for concurrent stimulation of other areas.

(e) Since it is held by the hands, it may be difficult to maintain proper position for protection between the body and the mouth of the partners. It may slip easily out of the fingers and out of position.

(f) Since the user must hold it in place against the body of the receiving partner, the receiving partner's body movements must be restricted in order to maintain proper placement.

Certain medical masks have been proposed which would suffer distinct disadvantages if an attempt were made to use them for protection during oral sex.

Sachs, in U.S. Pat. No. 3,288,138 (1966), proposes a surgical mask molded in cupped shape to cover the nose, mouth, and chin. Breathing tubes aim air rearwards, to prevent it going upward and possibly fogging glasses.

Fisichella, in U.S. Pat. No. 4,323,063 (1982), proposes a medical face mask which is generally oval shaped, covering the nose, mouth, and chin, with a central transparent portion, designed to enhance verbal communication.

Lemelson, in U.S. Pat. No. 4,856,509 (1989), proposes a face mask and method, the mask being generally oval-shaped, covering the nose, mouth, and chin, and including a central portion containing germ-killers.

All three of these suffer similar disadvantages in relation to sexual protection.

(a) They are all designed primarily for medical purposes, to filter air-born particles, not body fluids in direct contact.

(b) Since they all cover the nose, a user must be able to breathe through them, therefore they cannot be made of latex, plastic wrap, or other materials known to prevent body fluid transfers. Sachs does avoid this problem by providing breathing tubes, but thereby incurs the problems of extra cost and claustrophobic feelings for the user.

(c) While engaged in oral sex, it is very difficult to breathe through a mask which covers the nose, even if its materials make it practical for that use.

(d) Sachs is constructed so as to be rigid, making it unusable for oral sex, which requires a flexible barrier.

(e) Fistchella and Lemelson both have loose central areas wide enough to get sucked into the mouth, causing (f) In addition, the central germ-killing portion proposed in Lemelson is too thick for the sensitive perception required in oral sex, and includes chemical coatings that could be potentially hazardous to the lips, tongue, mouths, and other sensitive body parts.

None of the available commercial products or proposed patents have yet adequately solved the problems associated with providing protection for certain forms of oral sex.

OBJECTS AND ADVANTAGES

Accordingly, several objects and advantages of the present invention are:

(a) to provide adequate protection against the transmission of Sexually Transmitted Diseases between partners engaging in cunnilingus or oral-anal sex;

(b) to provide a protective device which will prevent any contact of the mouth area with the genital areas of the partner;

(c) to provide a protective device which is comfortable, appealing and easy to use;

(d) to provide a protective device that covers the mouth and is attached to the head of the wearer rather than to the body of the partner;

(e) to provide a protective device which will be held on the face by ties or bands so as to keep the hands free during oral sex;

(f) to provide a protective device that will stay securely in place during use;

(g) to provide a protective device which allows for free movement of the mouth, tongue, and lips of the wearer;

(h) to provide a protective device which will not trigger a gag reflex or a feeling of suffocation and which will allow for easy swallowing and easy breathing while in use;

(i) to provide a protective device which allows for free movement of the body of the partner receiving stimulation;

(j) to provide a protective device of sufficient sensitivity to allow easy location of and adequate stimulation of the partner's clitoris or other sensitive areas;

(k) to provide a protective device that is simple and comparatively inexpensive to manufacture;

(l) to provide a protective device which will give adequate coverage of the mouth area without wasting materials in unnecessarily covering the cheeks;

(m) to provide a protective device which can be manufactured with or without artificial flavors, to suit the tastes of consumers.

Further objects and advantages of my invention will become apparent from a consideration of the drawings and ensuing description.

DESCRIPTION OF DRAWINGS

FIG. 2 shows the protective mask with curved shield in a top perspective view.

FIG. 3 shows the upper ring of the holder assembly in a top perspective view,

FIG. 4 shows the curved shield in a top persective view.

FIG. 5 shows the lower ring of the holder assembly in a top perspective view.

FIG. 6 shows a cross section of the two rings of the holder assembly with the shield in place.

FIG. 7 shows an alternative method for attaching the shield to the holder assembly FIG. 8 shows a curved variation of the holder assembly in a side perspective view.

Figure 1:
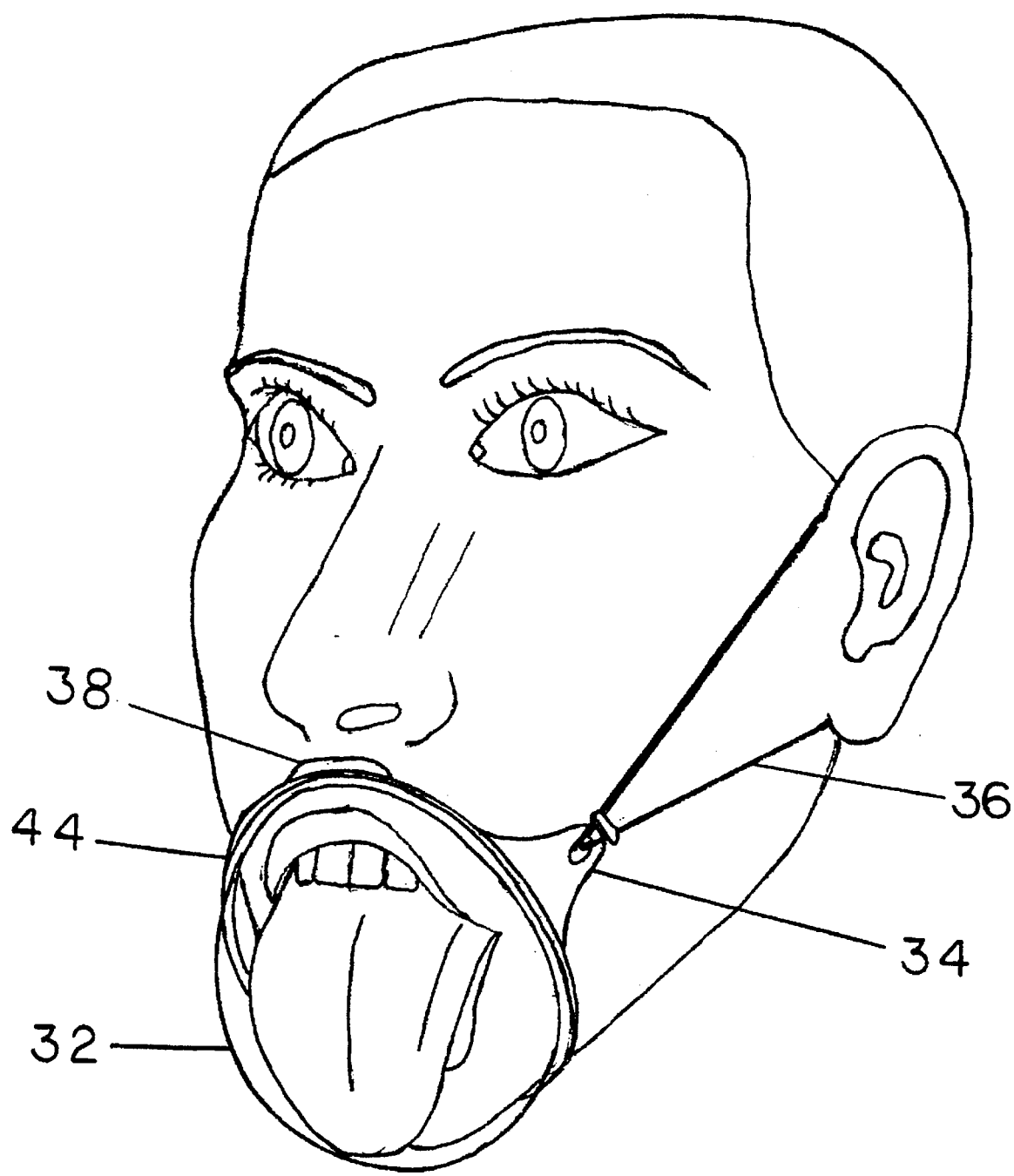
FIG. 1 shows the protective mask in place on the face of the wearer with mouth open.

REFERENCE NUMERALS IN DRAWINGS 30U upper ring of holder
30L lower ring of holder
32 shield
34 eyelet
36 ear loop
38 nose cushion
40 rim
42 membrane
44 holder assembly
46 trough
48 securing ring

SUMMARY

The protective mask consists of a disposable shield held in place over the mouth either alone or with a holder assembly. The holder assembly grasps the outside rim of the shield and attaches to the face with ear loops, ties, headband, or other means. The shield alone may be similarly attached to the head without any holder assembly.

DESCRIPTION

A preferred embodiment of the invention is illustrated in FIG. 1 in place on the face of the wearer with mouth open and in FIG. 2 by itself. This embodiment of the protective mask comprises a coupling device or holder assembly 44 and a shield 32 that can be held in place on the face of the wearer with ear loops 36 or other mounting devices.

FIGS. 3 to 6 show more details of the structure of this embodiment. Holder assembly 44 comprises two rings that interlock: an upper ring 30U and a lower ring 30L. These peripheral frame members are substantially circular and dimensioned to continuously surround the lips of a user during movements of the mouth. They are further formed for positioning beneath the nasal cavities of the user.

FIG. 3 shows upper ring 30U, which includes two eyelets 34 positioned on either side of upper ring 30U, forward of the latitudinal mid-line of upper ring 30U. Eyelets 34 can be made of the same material as upper ring 30U and molded with it in one piece or made of some other material and mounted to upper ring 30U. Two earloops 36 attach to eyelets 34 with knots, adhesives, wire, plastic, molded construction, or other means. Earloops 36 are cord members formed to mount to the ears of the user. Earloops 36 can be made of rubber or other elastic material. They are sufficiently large to reach over the ears of the wearer comfortably and snugly. Together, eyelets 34 and earloops 36 form a pair of mounting devices coupled to opposite sides of upper ring 30U. Upper ring 30U also includes a nose cushion 38 mounted to it and positioned in the center front. Nose cushion 38 is formed to provide protective cushioning between the user's nose and upper ring 30U and can be made of soft rubber or soft plastic or fabric, or any soft, sufficiently cushioning material.

FIG. 4 shows shield 32 with its component parts, a rim 40 and a membrane 42. Rim 40 is an annular, substantially non-permeable, semi-flexible peripheral frame member defining a passageway therethrough and dimensioned to continuously surround the lips of a user during movements of the mouth. Rim 40 is substantially thicker than membrane 42. Membrane 42 is substantially non-permeable, relatively thin, pliable, distendable, and is mounted to rim 40, extending across the passageway to provide a pliable barrier over the lips and mouth. Membrane 42 is substantially more flexible and pliable than rim 40. Membrane 42 is preferably made of latex rubber, pliable polymer, synthetic polymeric material, or other material that is sufficiently thin and flexible yet impermeable to body fluids. In this embodiment, membrane 42 has a convex shape.

FIG. 5 shows lower ring 30L, which is annular, uniform, and designed to continuously perimetrically engage upper ring 30U, removably coupling them together with shield 32 interposed. It has a trough 46 which is a circumferentially extending cavity. In this embodiment, the transverse cross-sectional dimension of the cavity is C-shaped and formed to removably receive the permetric transverse cross-sectional dimension of upper ring 30U while removably retaining shield 32 therebetween.

Upper ring 30U and lower ring 30L are preferably made of plastic sufficiently rigid to snap together and hold the shield and also flexible enough to bend comfortably on the face of the wearer. It is possible to construct the rings 30U and 30L out of other materials having those characteristics.

FIG. 6 shows a cross section of rings 30U and 30L interlocked with membrane 42 between them and rim 40 on the outside of the rings. Rim 40 is thick enough that it cannot slip or be pulled through rings 80U and 80L when they are interlocked.

There are many possible variations of embodiment.

Any embodiment of the shield could be used without any coupling device or holder assembly 44. In that case, rim 40 of the shield would be semi-flexible, yet sufficiently rigid to support membrane 42 during use.

In another alternative embodiment, rim 40 of the shield could snap directly into upper ring 30U, eliminating the need for lower ring 30L of the coupling device.

FIG. 7 shows an alternative shape for the coupling device and an alternative method for removably coupling shield 32 thereto. In this embodiment, upper ring 30U contains trough 46, which is designed to continuously perimetrically receive rim 40. Securing ring 48 is annular and dimensioned to continuously surround trough 46 while removably retaining rim 40 therewithin. This embodiment can also be used without securing ring 48. In that case, rim 40 and trough 46 would be dimensioned such that rim 40 would be retained firmly and securely within trough 46 during use, without need for any securing ring 48.

FIG. 8 shows an alternative embodiment with holder assembly 44 curved so that it does not lie all in the same plane. This variation could be used with any embodiment. Entire holder assembly 44 could be curved in this manner. The shield used alone without a coupling device could be curved in this manner. The shield and upper ring 30U designed to be used without any lower ring 30L could be curved in this manner. Any embodiment of this invention could be curved in this manner or in any other that would substantially conform to the face of the wearer or provide other advantages.

A substantially flat shield could be used in any embodiment of the invention, in place of the convex-shaped shield illustrated here.

Other cord members, such as ties or a continuous headband formed to extend around the backside of the user's head could be substituted for earloops 36 to engage a portion of the user's head and retain the mask against the face. Any of these mounting devices could be attached directly to the shield instead of to the coupling device.

Any sort of fastenings could be substituted for eyelets 34, as long as they were sufficient to affix the ear loops 36 or other mounting devices to the protective mask or to the coupling device.

Any embodiment of the protective mask may be made without nose cushion 38.

From the description above, a number of advantages of my protective mask become evident:

(a) The protective mask provides substantial protection against STDs for both partners engaging in oral-genital or oral-anal sex.

(b) The protective mask is easy to use. The interlocking rings simply snap together to hold the shield. It is easy to fit into place on the face with ear loops, ties, or a headband.

(c) The protective mask is comfortable to use. With the protective mask in place, the wearer can still enjoy completely free movement of the mouth and lips. The wearer can breathe and swallow easily while it is in place. The wearer can close the mouth periodically to rest the jaw or swallow.

(d) The rim holds the shield taut enough to keep it outside the mouth, eliminating gagging problems.

(e) The shield easily stays in proper position over the mouth because of the sturdy structural support of the rim, with or without the holder assembly.

(f) The protective mask stays in place securely with ties, ear loops, or headband.

(g) By being attached to face of wearer, the protective mask allows free movement of the body of the partner receiving stimulation, while providing protection for both partners.

(h) The shield is thin enough to allow for easy location and stimulation of sensitive areas.

(i) The protective mask provides economical protection, completely covering the mouth without wasting any materials in unnecessarily covering the cheeks.

(j) The holder assembly is durable, and may last for years through many uses. The disposable component, the shield, is simple and inexpensive to manufacture. This makes it viable to consumers as an affordable, disposable article.

OPERATION

In every embodiment of the protective mask there is a disposable shield which is secured over the mouth of the wearer by some means. In some embodiments the shield alone is fitted over the mouth. In some embodiments there is some manner of holder that grips the disposable shield and holds it in place over the mouth. There are various means of attaching the shield or its holder to the head of the wearer, but they all operate in essentially the same manner.

The protective mask is held on the face in various ways. In the preferred embodiment shown in FIGS. 1 to 6, shield 32 is held by holder assembly 44. One places shield 32 on top of lower ring 30L so that rim 40 extends just outside the circumference of lower ring 30L. Upper ring 30U snaps snugly into place in trough 46 of lower ring 30L, securing shield 32 in place. Rim 40 remains outside the circumference of holder assembly 44, assuring that shield 32 cannot slip out of holder assembly 44. Now gripping shield 32, holder assembly 44 is fitted up to the mouth of the wearer with nose cushion 38 placed just below the nasal septum. Ear loops 36 are looped over the ears of the wearer, and the mouth protector is now in place.

Nose cushion 38 protects the sensitive area of the nasal septum of the wearer from pressure while the protective mask is in use.

After use, disposal of shield 32 is easy. Upper and lower rings 30U and 30L are snapped apart and shield 32 is removed. When not in use holding a shield, upper and lower rings 30U and 30L can be snapped together for storage.

In the embodiment shown in FIG. 7, rim 40 slips into trough 46 and is held in place by securing ring 48. Or if no securing ring 48 is needed, rim 40 simply snaps into trough 46 and stays securely there during use.

In the embodiment where shield 32 is used alone without any coupling device or holder assembly 44, shield 32 is positioned directly over the mouth of the user, below the nasal cavitites, and retained against the user's face by the mounting devices: earloops 36, headband, or other suitable cord members.

All the variations in the shape or construction of the protective mask operate in substantially the same manner.

CONCLUSION, RAMIFICATIONS, AND SCOPE OF INVENTION

Accordingly, the reader will see that the protective mask of this invention provides protection against transmission of STDs that is comfortable, economical, and easy to use. It completely covers the mouth area of the wearer, protecting both partners engaging in oral sex. The protective mask has further advantages in that it stays securely in place over the mouth of the wearer while allowing for easy breathing and swallowing and completely free movement of the wearer's lips and tongue;

it keeps the wearer's hands free to use for concurrent stimulation of other areas;

it allows for free movement of the body of the partner receiving stimulation while still providing adequate protection for both partners;

it provides a protective barrier that is thin enough to allow location and stimulation of sensitive areas;

it completely covers the mouth and lips of the wearer without wasting materials in unnecessarily covering the cheeks; and it provides a simple disposable shield component that is inexpensive to manufacture.

Although the description above contains many specificities, these should not be construed as limiting the scope of the invention, but as merely providing illustrations of some of the presently preferred embodiments of this invention. For example, the materials herein specified are examples and any ones having desired characteristics may be substituted for those specifically identified. The shape and dimensions of various embodiments may be varied within the scope of the invention. The protective mask may be made in different colors, patterns, textures, flavors, and of varied materials. It can be made hinged or flexible enough to fold down to a smaller size for easier carrying. It can be made with or without a nose cushion. It can be held on the face by various means. The shields may attach to the holder assembly by other means, etc. A limited number of embodiments of the invention have been described in some detail. It is intended that the foregoing disclosure and drawings shall be considered only as illustrations of the principles of the invention.

Accordingly, the scope of the invention should be determined not by the embodiments illustrated, but by the appended claims and their legal equivalents.

I claim:

1. A protective mask comprising:

a substantially non-permeable, semi-flexible peripheral frame member defining a passageway therethrough, and dimensioned to continuously surround the lips of a user during movements of the mouth, said frame member further formed for positioning beneath the nasal cavities of said user, said frame member further formed to be substantially narrow and sufficiently rigid;

a substantially non-permeable, relatively thin, pliable and distendable membrane mounted to said frame and extending across said passageway to provide a pliable barrier over said lips and said mouth, said membrane being substantially more flexible and pliable than said frame member a means for removably attaching said membrane to said frame;

a pair of mounting devices coupled to opposite sides of said frame, each mounting device being formed for engaging a portion of said user's head for retaining said mask against said face underneath said nasal cavities.

2. The protective mask as defined in claim 1 wherein, said membrane comprises a pliable polymer.

3. The protective mask as defined in claim 1 wherein, said membrane comprises latex.

4. The protective mask as defined in claim 1 wherein, said mounting devices include eyelets mounted to said frame member and a cord member mounted to each eyelet for engaging said user's head for mounting thereto.

5. The protective mask as defined in claim 4 wherein, each cord member is formed to mount to a respective ear of said user.

6. The protective mask as defined in claim 4 wherein, said cord member includes one end mounted to one said eyelet, and an opposite end mounted to the other said eyelet, said cord member formed to extend around the backside of said user's head for mounting engagement therewith.

7. The protective mask as defined in claim 1 wherein, said frame member is formed to conform to said user's face.

8. The protective mask as defined in claim 1 wherein, said membrane is convex-shaped.

9. A prophylactic protective mask comprising:

a peripheral frame member defining a passageway therethrough, and dimensioned to continuously surround the lips of a user during movements of the mouth;

a substantially non-permeable, relatively thin, pliable and distendable membrane formed to extend across said passageway;

a coupling device removably coupling said membrane to said frame member to provide a pliable barrier over said lips and said mouth; and a pair of mounting devices coupled to opposite sides of said frame, each mounting device being formed for engaging a portion of said user's head for retaining said mask against said face.

10. The protective mask as defined in claim 9 wherein, said coupling device is formed to continuously perimetrically engage said frame member such that said engaging portions of said membrane are interposed between said frame member and said coupling device.

11. The protective mask as defined in claim 10 wherein, said coupling device provides a circumferentially extending cavity having a transverse cross-sectional dimension formed to removably receive the perimetric transverse cross-sectional dimension of said frame member in a manner removably retaining said engaging portions of said membrane therebetween.

12. The protective mask as defined in claim 11 wherein, said cross-sectional dimension of said cavity is C-shaped.

13. The protective mask as defined in claim 9 wherein, said frame member is further formed for positioning beneath the nasal cavities of said user.

14. The protective mask as defined in claim 13 further including:

a nose cushion mounted to said frame member and formed to provide protective cushioning between the user's nose and said frame member.

15. The protective mask as defined in claim 9 wherein, said membrane is substantially more flexible and pliable than said frame member.

16. The protective mask as defined in claim 9 wherein, said frame member is formed to conform to said user's face.

17. The protective mask as defined in claim 9 wherein, said membrane is convex-shaped.

18. The protective mask as defined in claim 9 wherein, said frame member is annular.

19. The protective mask as defined in claim 9 wherein, said mounting devices include eyelets mounted to said frame member and a cord member mounted to each eyelet for engaging the head for mounting thereto.

* * * * *